United States Patent [19]

Weber et al.

[11] 4,102,339
[45] Jul. 25, 1978

[54] DEVICES FOR TENSIONING SURGICAL APPLIANCES

[75] Inventors: Bernhard Georg Weber, St. Gall; Beat Flury, Hölstein, both of Switzerland

[73] Assignee: Synthes AG, Switzerland

[21] Appl. No.: 778,374

[22] Filed: Mar. 17, 1977

[30] Foreign Application Priority Data

Mar. 26, 1976 [CH] Switzerland .................. 3801/76

[51] Int. Cl.² ...................... A61B 17/18; A61F 5/04
[52] U.S. Cl. ...................... 128/92 E; 128/84 R; 128/92 D
[58] Field of Search ........... 128/92 D, 92 E, 92 R, 128/92 G, 92 A, 83, 84 R, 84 B

[56] References Cited

U.S. PATENT DOCUMENTS

| 3,386,437 | 6/1968 | Treace ................. | 128/92 D |
| 3,400,711 | 9/1968 | Hux et al. ............ | 128/92 D |
| 3,709,219 | 1/1973 | Halloran ............. | 128/92 E X |

FOREIGN PATENT DOCUMENTS

| 394,479 | 11/1965 | Switzerland ......... | 128/92 D |
| 1,118,773 | 7/1968 | United Kingdom ..... | 128/92 R |

*Primary Examiner*—Ronald L. Frinks
*Attorney, Agent, or Firm*—McGlew and Tuttle

[57] ABSTRACT

A device for tensioning a surgical appliance is disclosed. The device comprises two elongate lever elements, anchor means articulated to a first end portion of one of the lever elements and adapted to be attached by a cortical screw to a bone fragment on one side of a fracture, and a hook element provided on a first end portion of the respective other lever element and adapted to be engaged with a plate member attached to a bone fragment on the respective other side of the fracture. The other end portions of the two lever elements are articulatedly intercoupled by means to exert a force between the two lever elements and to indicate the magnitude of that force. A threaded member is rotatably retained in each of two guide elements to interconnect intermediate portions of the two lever elements. The guide elements are pivotably supported on respective ones of the two lever elements and the threaded member is rotatably adjustable to enable a surgeon to vary the spacing between the respective first end portions of the two lever elements. Preferably, the hook element is pivotable between two alternative positions, in a first of which it is supported to exert traction on the plate member and in the second of which it is supported to exert distraction on the plate member.

14 Claims, 2 Drawing Figures

DEVICES FOR TENSIONING SURGICAL APPLIANCES

BACKGROUND OF THE INVENTION

The present invention relates to a device for tensioning a surgical appliance and relates particularly to such a device for tensioning compression plates used in the treatment of bone fractures. p Known for the tensioning of surgical compression plates is a plate tensioning device provided with a perforated strip element or strap, through which a cortical screw is screwable into one of two parts of a broken bone which have to be pressed together. This tensioning device is provided with a hook for hooking into the compression plate attached to the respective other part of the broken bone and with a tensioning screw to draw the hook towards the strap.

The mode of construction of this known tensioning device is very simple: A carrier, in which a screw thread is cut with an axis parallel to the strap, is connected fast with the strap and arranged to protrude at right angles from it. Engaging this thread is a tensioning screw which is so arranged that its head is on the side of the carrier remote from the strap. Mounted between the screw head and the carrier is a slide, which is secured against rotation by two pins, which are displaceably guided in bores of the carrier. This slide is provided with a draw hook for tightening the compression plate. This construction displays different disadvantages: Due to the fact that the slide is connected to the screw head at one place and engages at the compression plate at another plate, tilting forces arise, which can cause the slide to become wedged fast, so that the surgeon cannot ascertain on tightening of the tensioning screw whether the force exerted by him serves to overcome the friction forces provided by the wedging action or to exert compression on the separate parts of the fractured bone. He lacks the necessary information on the compressive force acting on the fracture location. A further disadvantage is that the hook, which is connected fast with the slide after the fastening of the strap of the tensioning device by means of the cortical screw, may be displaced only in the direction of the tensioning screw. Thus, the hook can no longer be displaced in a direction perpendicular to the screw. A third disadvantage is that with the tensioning screw screwed in, the cortical screw is not accessible, so that during the screwing-on of the strap and during the unscrewing, and also during any adjustment such as loosening the tensioning device which may become necessary, the tensioning screw with its free end remote from the head must not then project out of the threaded bore.

It is an object of the present invention to provide a tensioning device for a surgical appliance in which some at least of the aforementioned disadvantages are substantially reduced.

SUMMARY OF THE INVENTION

According to the present invention, there is provided a device for tensioning a surgical appliance, comprising two elongate lever elements, anchor means articulated to a first end portion of one of the lever elements and adapted to be attached to a bone fragment on one side of a fracture, a hook element provided on a first end portion of the respective other lever element and adapted to be engaged with a plate member attached to a bone fragment on the respective other side of the fracture, force generating means coupling each of the respective other end portions of the two lever elements to exert a force between the two lever elements and being provided with means to indicate the magnitude of the force exerted, a threaded member rotatably retained in each of two guide elements to interconnect intermediate portions of the two lever elements, the guide elements each being pivotably supported on a respective one of the two lever elements and the threaded member being rotatable to vary the spacing between the respective first end portions of the two lever elements.

Preferably, the threaded member is provided with two mutually oppositely directed threaded portions and each of the two guide elements is provided with an internally threaded portion adapted to engage at least one of the two threaded portions of the threaded member.

BRIEF DESCRIPTION OF THE DRAWINGS

An embodiment of the invention will now be more particularly described by way of example with reference to the accompanying drawing, in which.

DESCRIPTION OF THE PREFERRED EMBODIMENT

Figure 1:
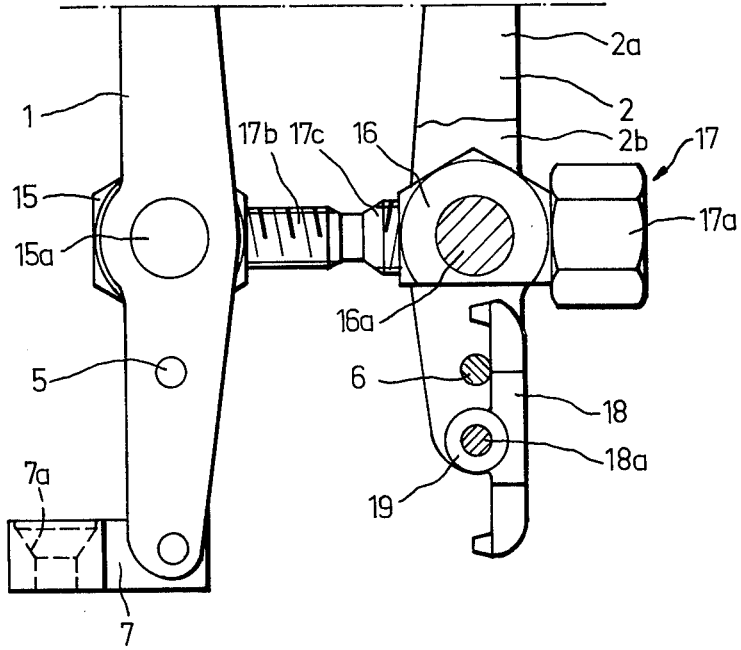
FIG. 1 shows partly in section a side elevation of a tensioning device embodying the invention and wherein individual parts of two levers of the device are shown broken away.

Referring now to the accompanying drawing, FIG. 1 shows a tensioning device embodying the invention and which comprises a first elongate lever element 1 and a second elongate lever element 2. Each of these lever elements comprises two identical limbs which are connected with each other by riveted webs 3, 4, 5 and 6. In FIG. 1, one piece of the limb 2a of the lever element 2 has been removed, so that part of the respective other limb 2b become visible in the drawing. Anchor means in the form of a perforate strip element 7, which is provided with a hole 7a for receiving a cortical screw, is articulatedly connected to a free end portion of the lever element 1. The strip or strap element 7 extends between the two limbs of the lever element 1. The respective other end portion of the lever element 1 is articulatedly connected with one end portion of the lever element 2 by way of force indicator means indicated generally by the reference numeral 8. The force indicator means 8 comprises two sleeves 9 and 10, one of which extends telescopically into the other, and is arranged to indicate pressure. The relative position of the two sleeves 9 and 10 may be read off on marking lines 9a. A rod 11 is proved at each end with a head 11a to restrain the two sleeves 9 and 10 from sliding apart. The sleeve is articulatedly connected to the lever element 1 by means of an axle spigot or pin 13 and the sleeve 10 is similarly connected to the lever element 2 by means of an axle spigot or pin 14. As shown in FIG. 1, force generating means in the form of a resilient element 12 urges the upper end portions of the two lever elements 1 and 2 apart from one another. Thus, the spring element 12 operates as a compression spring. A guide element in the form of an internally threaded nut 15, provided with two stub axles 15a, is journalled to be freely rotatable between the limbs of the lever element 1. Another guide element in the form of a nut 16 with two stub axles 16a is journalled to be freely rotatable in the same mode and manner between the limbs 2a and 2b of the lever element 2, wherein the axes of rotation of the stub axles extend perpendicularly to the axes of the corresponding thread axis. An externally threaded member in the form of a tensioning screw 17 provided with a head 17a is screwed into the two threaded nuts 15 and 16. As one can see in FIG. 1 of the drawing, the screw 17 has two oppositely-handed threaded portions. Thus, at the free end of the screw 17, a right-hand threaded portion 17b is provided and, between the thread and the head 17a, a left-hand threaded portion 17c is provided. The diameter of the threaded portion 17c is so much greater than the diameter of the threaded portion 17b that the latter may be pushed through the internally threaded bore of the larger nut 16. A double-ended hook 18 is mounted to be pivotable about a stub axle 18a. Thus, the hook 18 is articulatedly connected to the free end of the lever element 2, and the hook 18 is restrained from freely swinging to and fro by an annular spring 19.

In use, the plate tensioning device is attached by a cortical screw 20 to one part 21a of a broken bone after a compression plate 22 has already been attached at the respective other part 21b of the broken bone by several cortical screws 23. The attachment of the tensioning device has to be so carried out by the surgeon that the hook 18 can be engaged with at least the last hole of the plate 22, which can then be drawn towards the anchorage provided by the strap 7. The hook 18 is engaged with an appropriate hole in the plate 22, which is drawn towards the strap 7 by turning the tensioning screw 17 until the two bone pieces 21a and 21b on opposite sides of the fracture abut against each other. On further tensioning, not only is a pressure now generated at the fracture location, but the plate spring element 12 is also compressed at the same time, so that the sleeves 9 and 10 telescope relative to one another. The pressure here may be read off at the marking lines 9a, when the tensioning device has previously been appropriately calibrated and the marking lines 9a have been correspondingly inscribed. When the requisite compression pressure is attained, the plate 22 is attached as usual by further screws (not shown) to the piece 21a of the broken bone, whereupon the tensioning device may then be removed.

On the hook 18 being pivotably displaced through 180° in the clock-wise sense relative to the position shown in the drawing, the device may be utilized for distraction, that is for pushing bone fragments apart from one another. In these circumstances, the compression spring 12 may be replaced by a tension spring.

As one can recognize from the preceding, the tensioning direction of the device is no longer determined by the plane, parallel to the axis of the tensioning screw, of the support surface of the perforated strap 7, but it is free, which is a further significant advantage, apart from reduction or avoidance of some at least of the previously mentioned disadvantages.

Figure 2:
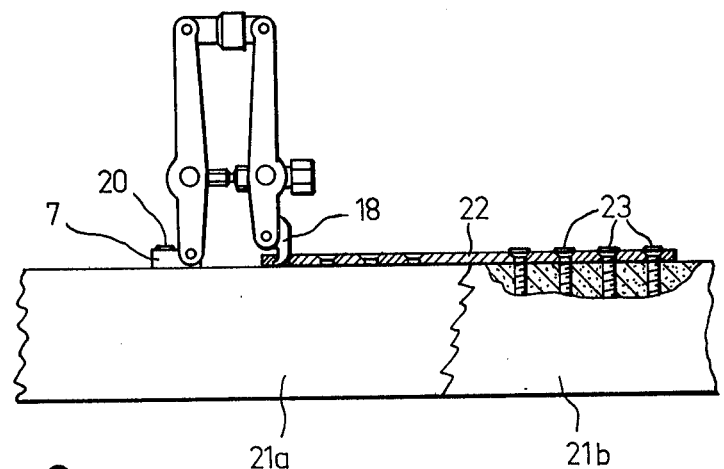
FIG. 2 shows on a smaller scale the tensioning device shown in FIG. 1 when attached to a bone, together with a tensioning plate.

The force generating means in the preferred embodiment is in the form of a compression spring 12. However, in some applications the spring 12 may be replaced by a pneumatic cylinder or by an hydraulically operable device to generate a force urging the upper end portions of the lever elements shown in FIGS. 1 and 2 apart from one another.

We claim:

1. A device for tensioning a surgical appliance, said device comprising in combination:

a. a first elongate lever element having first and second end portions;
  b. a second elongate lever element having first and second end portions;
  c. anchor means articulatedly connected to said first end portion of said first elongate lever element and adapted to be attached by screw means to a bone fragment on one side of a bone fracture;
  d. a hook element provided on said first end portion of said second elongate lever element and adapted to be engaged with a plate member attached to a bone fragment on the respective other side of said bone fracture;
  e. force generating means coupling the respective second end portions of said first and second elongate lever elements to generate a force acting therebetween;
  f. force indicator means operatively associated with said force generating means to indicate the force exerted thereby on said first and second elongate lever elements;
  g. two guide elements each articulatedly supported on a respective one of said first and second elongate lever elements at portions thereof intermediate said first and second end portions;
  h. a threaded member rotatably retained in each of said two guide elements to interconnect said first and second elongate lever elements, said threaded member being rotatable to vary the spacing between the respective first end portions of said first and second elongate lever elements.

2. A device as defined in claim 1, wherein said force indicator means is articulatedly connected to each of said first and second elongate lever elements.

3. A device as defined in claim 1, wherein said anchor means comprises a perforate strip element.

4. A device as defined in claim 1, wherein said threaded member is provided with two mutually oppositely directed threaded portions, and wherein each of said two guide elements is provided with an internally threaded portion adapted to engage at least one of said two threaded portions of said threaded member.

5. A device as defined in claim 4, wherein said two threaded portions are of different diameters.

6. A device as defined in claim 1, wherein the force generating means comprises a spring, and wherein the force indicator means is adapted to indicate pressure and comprises two sleeves each encompassing said spring and each articulatedly connected to a respective one of said first and second elongate lever elements, and a limit rod retaining said sleeves in telescopic relationship one with the other.

7. A device as defined in claim 1, wherein said hook element is articulatedly connected to said first end portion of said second elongate lever element.

8. A device as defined in claim 7, wherein said hook element comprises a first hook and a second hook, said hook element being pivotably mounted selectively to engage said first hook with said plate member to exert traction thereon and to engage said second hook with said plate member to exert distraction thereon.

9. A device as defined in claim 8, wherein said hook element is supported by said first end portion of said second elongate lever element to be pivotably displaceable through 180° about an axis extending substantially parallel to the axis of pivotation of said elongate lever element about said intermediate portion.

10. A surgical tensioning device comprising a first and second lever means, an anchor means pivotally connected to one end of one of said lever means, a hook means pivotally connected to a corresponding end of other lever means, means for articulatedly connecting the other ends of the respective levers, and means connected intermediate the ends of said first and second lever for adjusting the spacing between said anchor means and hook means.

11. A surgical tensioning device as defined in claim 10 wherein said articulatedly connecting means includes a force generating means for generating a force acting on the respective said other ends of said respective levers.

12. A surgical tensioning device as defined in claim 11 and including an indicating means operatively associated with said force generating means for indicating the amount of force exerted by said force generating means.

13. The surgical tensioning device as defined in claim 11 wherein said force generating means comprises a tension spring.

14. The surgical tensioning device as defined in claim 11 wherein said force generating means comprises a compression spring.

* * * * *